US009226535B1

(12) United States Patent
Thramann et al.

(10) Patent No.: US 9,226,535 B1
(45) Date of Patent: Jan. 5, 2016

(54) GARMENT TO FACILITATE NEEDLE ELECTRODE PLACEMENT FOR INTRAOPERATIVE MONITORING

(75) Inventors: Jeff Thramann, Longmont, CO (US); James Higgins, Phoenix, AZ (US)

(73) Assignee: SPECIALTYCARE IOM SERVICES, LLC, Nashville, TN (US)

( * ) Notice: Subject to any disclaimer, the term of this patent is extended or adjusted under 35 U.S.C. 154(b) by 638 days.

(21) Appl. No.: 13/566,529

(22) Filed: Aug. 3, 2012

Related U.S. Application Data

(63) Continuation of application No. 12/831,708, filed on Jul. 7, 2010, now Pat. No. 8,260,427.

(51) Int. Cl.
| | |
|---|---|
| *A61B 1/00* | (2006.01) |
| *A41D 13/12* | (2006.01) |
| *A61B 5/05* | (2006.01) |
| *A61B 17/34* | (2006.01) |
| *A61N 1/00* | (2006.01) |

(52) U.S. Cl.
CPC .................................. *A41D 13/1236* (2013.01)

(58) Field of Classification Search
CPC ............. A61B 5/0492; A61B 18/1477; A61B 18/1482; A61B 2018/1425; A61B 2018/0022; A61B 19/201; A61B 5/6804; A61B 17/062; A61N 1/36017; A61N 2/006; A61N 1/0456; A61N 1/08; A61N 1/36071; A61N 1/0551; A61N 1/36014; A61N 1/36021; A61N 1/0484; A61N 2/008; A61N 1/0452; A61N 1/0502; A61N 1/36057

USPC ................. 600/372–373, 386–390, 547, 554; 607/46, 115–116, 149
See application file for complete search history.

(56) References Cited

U.S. PATENT DOCUMENTS

| | | | |
|---|---|---|---|
| 4,729,377 A | 3/1988 | Granek et al. | |
| 5,390,671 A | 2/1995 | Lord et al. | |
| 5,693,018 A | 12/1997 | Kriesel et al. | |
| 5,858,001 A | 1/1999 | Tsals et al. | |
| 6,093,172 A | 7/2000 | Funderburk et al. | |
| 6,516,289 B2 | 2/2003 | David | |
| 6,695,860 B1 | 2/2004 | Ward et al. | |
| 2002/0058972 A1 | 5/2002 | Minogue et al. | |
| 2003/0212319 A1 | 11/2003 | Magill | |
| 2005/0010096 A1 | 1/2005 | Blackadar | |
| 2005/0054941 A1 | 3/2005 | Ting et al. | |
| 2005/0137662 A1* | 6/2005 | Morris et al. ............... 607/101 |
| 2006/0247733 A1 | 11/2006 | Amer | |
| 2007/0106343 A1 | 5/2007 | Monogue et al. | |
| 2007/0276213 A1 | 11/2007 | David et al. | |
| 2008/0097530 A1 | 4/2008 | Muccio et al. | |

(Continued)

FOREIGN PATENT DOCUMENTS

| | | |
|---|---|---|
| DE | 102004032410 | 1/2006 |
| WO | WO-2009134246 | 11/2009 |

OTHER PUBLICATIONS

International Search Report and Written Opinion dated Feb. 9, 2012 for PCT/US2011/040007. 8 pages.

*Primary Examiner* — Joseph Stoklosa
*Assistant Examiner* — Brian M Antiskay
(74) *Attorney, Agent, or Firm* — Perkins Coie LLP

(57) ABSTRACT

A garment is provided with a tube that may be used to facilitate placement of needle electrodes into a patient to facilitate intraoperative monitoring during surgical procedures.

20 Claims, 9 Drawing Sheets

(56) References Cited

U.S. PATENT DOCUMENTS

| | | |
|---|---|---|
| 2008/0154334 A1 | 6/2008 | Gavronsky |
| 2009/0012408 A1 | 1/2009 | Nagata et al. |
| 2009/0082694 A1 | 3/2009 | Poisner |
| 2009/0088652 A1 | 4/2009 | Tremblay |
| 2009/0124867 A1 | 5/2009 | Hirsh et al. |
| 2009/0124876 A1* | 5/2009 | Nakamura et al. ............ 600/345 |
| 2009/0234179 A1 | 9/2009 | Burnett et al. |
| 2010/0130847 A1* | 5/2010 | Dunagan ...................... 600/389 |
| 2011/0237924 A1 | 9/2011 | McGusty et al. |

* cited by examiner

GARMENT TO FACILITATE NEEDLE ELECTRODE PLACEMENT FOR INTRAOPERATIVE MONITORING

CLAIM OF PRIORITY UNDER 35 U.S.C. §§119, 120

The present application is a continuation of U.S. application Ser. No. 12/831,708, filed Jul. 7, 2010, now U.S. Pat. No. 8,260,427, titled Garment to Facilitate Needle Electrode Placement for Intraoperative Monitoring, which is incorporated herein by reference as if set out in full.

REFERENCE TO CO-PENDING APPLICATIONS FOR PATENT

The present Application for Patent is related to co-pending U.S. patent application Ser. No. 12/724,778, titled Somatosensory Evoked Potential (SSEP) Automated Alert System, filed Mar. 16, 2010, and incorporated herein by reference as if set out in full.

BACKGROUND

1. Field

The technology of the present application relates generally to intraoperative monitoring (IOM), and more specifically, to garments and methods of using the garments to facilitate placement of needle electrodes for IOM.

2. Background

During surgery, nerve damage is possible for a number of reasons. For example, one potential complication from surgery may include peripheral neuropathy related to surgical positioning that may in some cases be generally known as an iatrogenic injury. Intraoperative positioning nerve injuries are complications from surgery that may occur from extension or compression of peripheral nerves.

Nerve injuries may be preventable by monitoring nerves or muscle groups innervated by the nerves for degradation of conductivity or the like. Even though preventable in many instances, peripheral nerve injuries still occur during surgery.

Because positioning injuries occur, some surgeries include intraoperative monitoring ("IOM"). The goal of IOM is to identify changes in brain, spinal cord, and peripheral nerve function prior to irreversible damage occurring.

IOM typically includes using an evoked potential such as, for example, somatosensory evoked potentials (SSEP), brain stem auditory evoked potentials (BAEP), motor evoked potentials (MEP), and visual evoked potentials (VEP). Generally, the activity associated with evoked potentials are elicited/evoked from a time-locked peripheral stimulus, such as, for example, stimulus to the arms/legs for SEP, noise in the ear for BAEP, or light for VEPs. Electromyography (EMG) also is used extensively during operative cases. Scalp electroencephalography (EEG) provides data for analysis of more spontaneous global electrocortical activity. Scalp EEG also can be used to monitor cerebral function during carotid or other vascular surgery. In addition, EEG recorded directly from the pial surface, or electrocorticography (ECoG), is used to help determine resection margins for epilepsy surgery, and to monitor for seizures during electrical stimulation of the brain carried out while mapping cortical function.

Looking specifically at SSEP, SSEPs are recorded by stimulating peripheral afferent nerves, usually electrically, and the responses are recorded with the help of scalp electrodes. Because of the presence of nonspecific EEG background activity, the evoked potential must be averaged to improve signal-to-noise ratio.

In intraoperative use, the median, or ulnar nerves, at the wrist are the most common stimulation site for upper extremity monitoring. In the lower extremity, the posterior tibial nerve just posterior to the medial malleolus, or common peroneal at the politeal fossa, are used most commonly. Other sites that can be utilized include the ulnar nerve.

Needle electrodes generally are used as they are easier to apply than, for example, surface electrodes that would require the skin to be prepared prior to use. Recording electrodes are placed on the scalp and over the cervical spine. Additionally, electrodes can be placed at the Erb's point for upper extremity SSEP recording and over the lumbosacral spine for lower extremity recording.

FIG. 1 shows a typical measure SSEP waveform 100. Waveform 100 is known as an N20 waveform and relates to the negative peak of the potential occurring at approximately 20 milliseconds. The waveform 100 was generated by a peripheral nerve stimulator using a constant current stimulus output applied to the wrist of a patient. Other types of stimulators are possible as well, such as, for example, a voltage based stimulator, a magnetic based stimulator, etc. The waveform 100 was the measured response by an electrode placed on the skin surface or subdermally of the patient's head. In this case, an electrode 200 was placed about 4 cm up and 2 cm back from the top of the ear 202 of the patient 204 as shown in FIG. 2.

As can be appreciated, placement of the needle electrodes in the patient is a part of IOM. A certified or skilled IOM technician must be on-site in the operating room to insert the needle electrodes properly into the patient using conventional methodologies. The on-site skilled IOM technician increases the cost of IOM and often results in many surgeries being conducted without IOM due to their cost and lack of availability in some areas. In some instances, nerve injury may be prevented if IOM had been available. Therefore, there is a need in the art for devices, apparatuses, methods, and the like to facilitate placement of needle electrodes in IOM.

SUMMARY

Embodiments disclosed herein address the above stated needs by providing a garment having needle electrodes. The garment facilitates the implantation of needle electrodes for intraoperative monitoring during a surgical procedure. The garment is made from a fabric having a thickness separating a skin surface adapted to reside proximate to the skin of a patient and a top surface opposite the skin surface. At least one tube resides in the fabric between the skin surface and the top surface, the tube has a stop. A needle electrode cooperatively engages the tube such that the tube is adapted to receive the needle electrode and the needle electrode is adapted to be inserted through the skin of the patient. The needle electrode cooperatively engages a stop such that the needle electrode will be positioned proximate a nerve to be monitored stimulated.

DETAILED DESCRIPTION

The technology of the present application will now be described with reference to the attached figures. While the technology of the present application is described with reference to measuring a sensory evoked potential from a peripheral nerve in the wrist such as, for example, the median, or ulnar nerves, one of ordinary skill in the art will recognize on reading the disclosure that the technology of the present application may be used to facilitate stimulating or monitoring of other sites on the scalp, torso, legs, or the like, such as, for example, the posterior tibial nerve just posterior to the medial malleolus, or the common peroneal at the politeal fossa, the median and ulnar nerves at the wrist as well as over the thenar and hypothenar eminence, and others. In particular, the present application describes the technology in relation to a garment associated with the hand, wrist, or arm, such as, for example, a glove, a wrist band, a sleeve, or combination thereof. Whereas monitoring associated with the legs may use a garment such as, for example, a stocking or leggings, and monitoring associated with the head may use a garment such as, for example, a skull cap or the like. Additionally, other garments may include multiple pieces such as, for example, a shirt-like arrangement covering the torso, arms, neck, etc. or a full body suit as necessary or required. As such, and for convenience, the technology of the present application will be described with reference to particular exemplary embodiments. The word "exemplary" is used herein to mean "serving as an example, instance, or illustration." Any embodiment described herein as "exemplary" is not necessarily to be construed as preferred or advantageous over other embodiments unless specifically indicated as such. Thus, the examples provided should be considered illustrative of the technology of the present application and not limiting.

Figure 1:
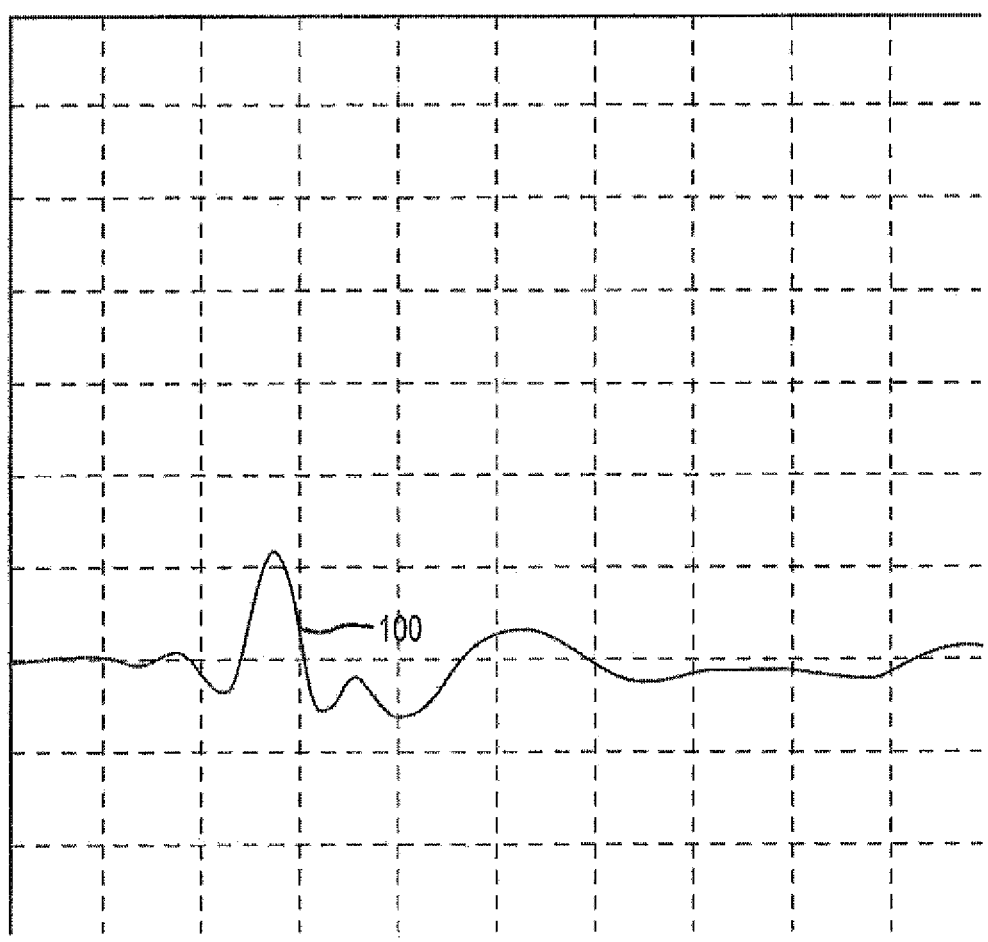
FIG. 1 is an exemplary waveform relating to a sensory evoked potential (SEP)
Figure 2:
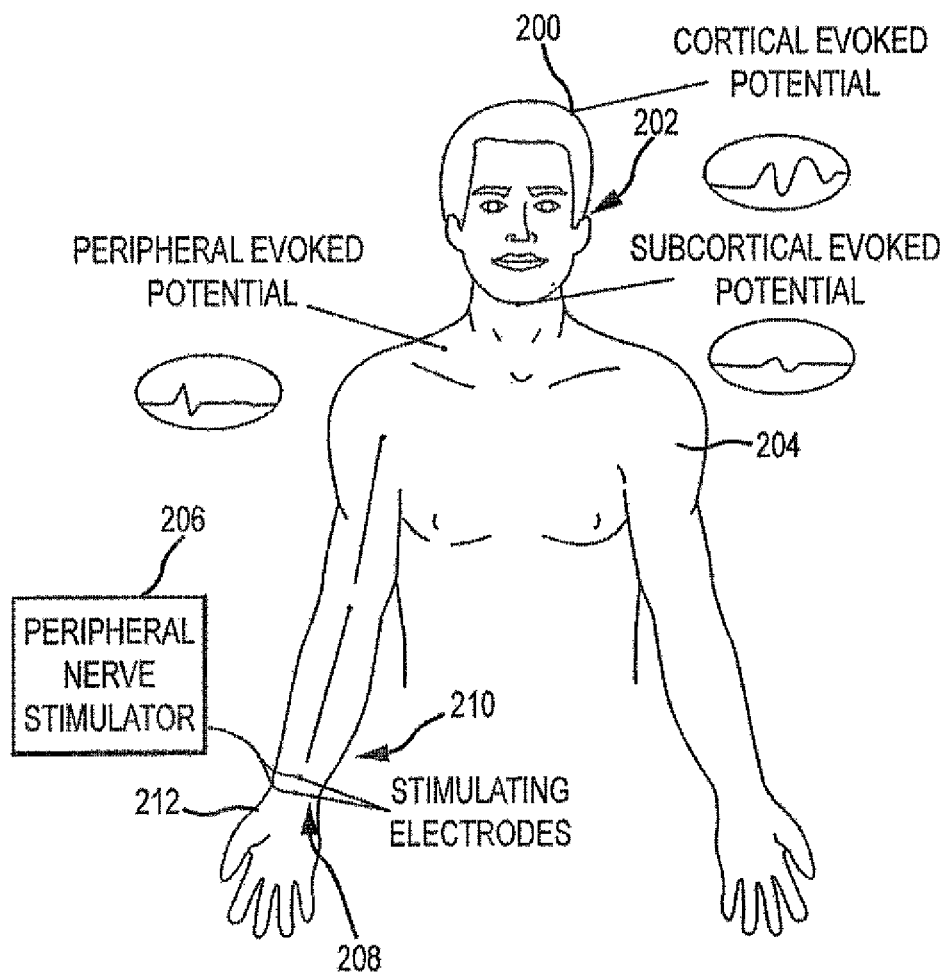
FIG. 2 is a functional block diagram showing a system useful in measuring the SEP of a patient.
Figure 3:
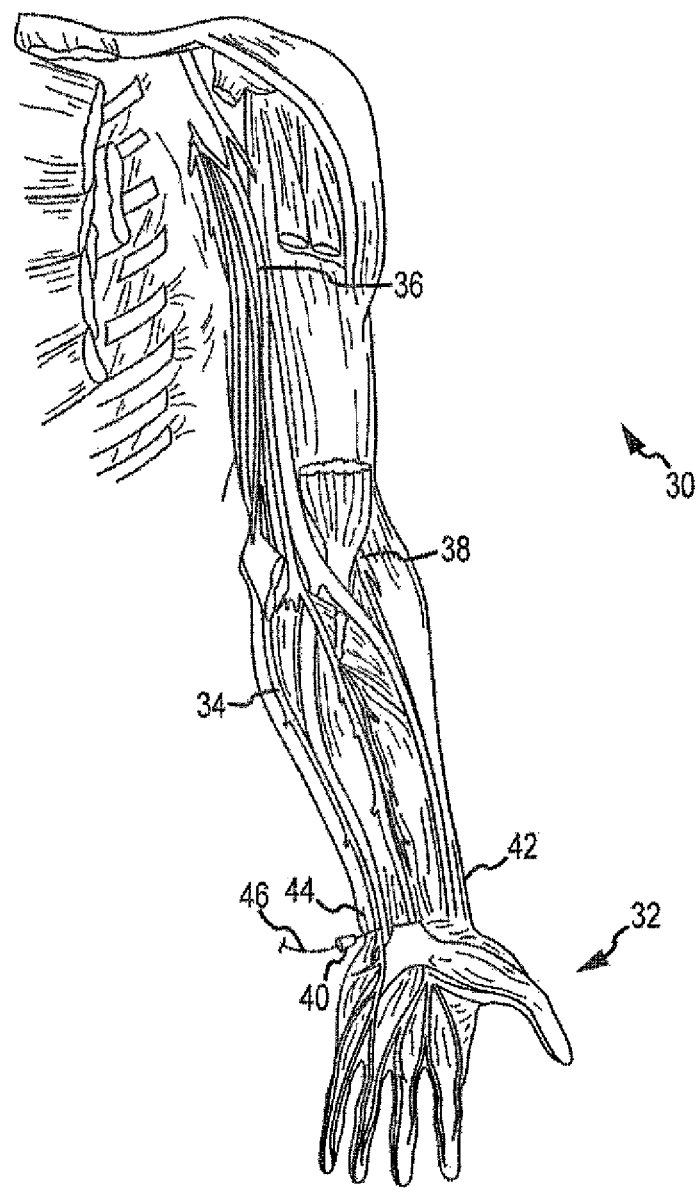
FIG. 3 is a diagram of representative anatomy associated with an arm and hand.

Referring now to FIG. 3, nerves associated with a typical arm 30 and hand 32 is provided. The arm 30 and hand 32 have nerves including the ulnar nerve 34, the median nerve 36, and the radial nerve 38. During conventional intraoperative monitoring (IOM) procedures, a needle electrode 40 is inserted through the skin 42 of the arm 30 or hand 32 into muscle tissue 44 and into contact with the associated nerve, such as, the ulnar nerve 34 as shown. Contact may include direct contact, but also may include a sufficiently proximate location to generate an acceptable SEP response at, for example, sensor 200. A lead 46 electrically couples needle electrode 40 to a peripheral nerve stimulator 206 as is conventionally known in the art. The peripheral nerve stimulator, such as, for example, a single channel constant current stimulus output may provide a stimulation signal to the monitored nerve. In the exemplary IOM procedure, the stimulation of the nerve 34 would evoke a corresponding electrical signal in the brain that may be measured; in other words, a sensory evoked potential. Changes in the sensory evoked potential may facilitate identification of nerve damage as further explained in co-pending U.S. patent application Ser. No. 12/724,778, titled Somatosensory Evoked Potential (SSEP) Automated Alert System.

Figure 4:
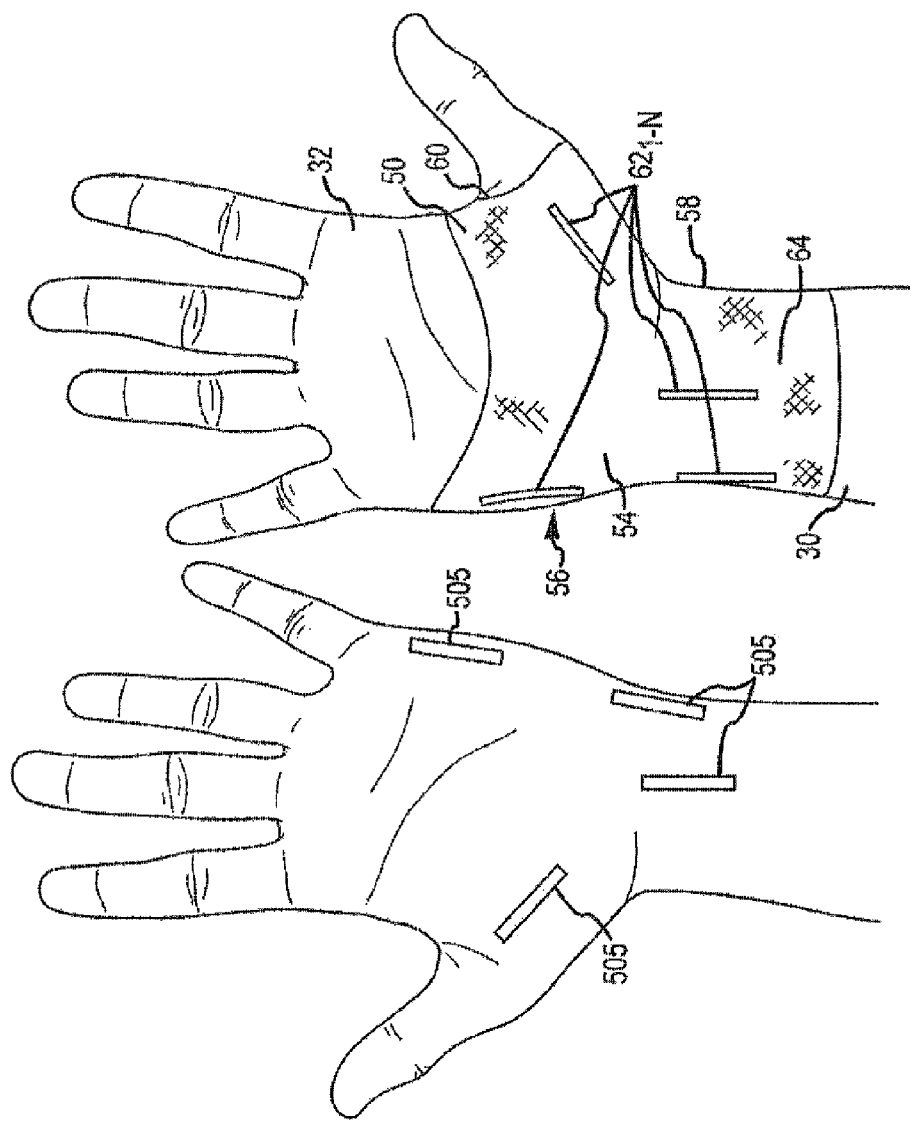
FIG. 4 is a top plan view of a garment consistent with the technology of the present application.

As can be appreciated, implanting needle electrode 40 requires a certain amount of precision and experience by a qualified technician. The precision and experience relates to properly locating the needle electrode 40 at an appropriate portion of the arm 30 or hand 32, angling the needle electrode 40 at an appropriate insertion angle α, and inserting the needle electrode 40 an appropriate amount such that the needle electrode 40 can stimulate the nerve, such as, nerve 34. The technology of the present application removes some of the experience a technician would require by providing a garment 50 as shown in FIG. 4. Garment 50 wraps about hand 32 and a portion of arm 30. Garment 50 includes, for example, a palm portion 54, a back of the hand portion 56 opposite the palm portion 54, a wrist portion 58, and a thumb portion 60. As shown, garment 50 is a partial glove and wrist band type of garment, but could be, for example, a complete glove having a pocket for the fingers or individual finger sleeves. The fit of the garment 50 provides an orientation of the garment 50 against the hand 32 and a wrist of the arm 30. In this case, for example, the wrist portion 58 and the thumb portion 60 provide a particular orientation. Other garments may have other markings and devices. For example, a legging may have an opening for the knee of a patient to provide proper orientation. Other garments may have instructions, such as, for example, a forearm sleeve may indicate that one opening should be oriented 2 cm from the wrist and the opposite opening should be oriented 1 cm from the elbow, etc.

Garment 50 being an orientable garment can be marked with electrode sites $62_{1-n}$ of which 4 electrode sites are provided in the present example and will be further explained below. In this case, the wrist portion and thumb portion facilitate proper orientation of the electrode sites $62_{1-n}$. Having multiple electrode sites also facilitates identifying which of the available inserted electrodes has the best connectivity between the electrode and the nerve being stimulated. Also, in the event one electrode site was not available due to, for example, an intravenous arterial line, alternative electrode sites would be readily available.

The garment 50 also may have additional markings or gaps as required by the particular operation that is being performed. For example, as shown, garment 50 may have an opening 64 in the wrist portion 58 such that the anesthesiologist, nurse, surgeon or other personnel may access the arterial line for pharmaceutical administration or the like. Electrode sites $62_{1-n}$ may provide for needle electrodes, surface electrodes, or other electrodes as may be known. While the present application is generally described with respect to needle electrodes, surface electrodes may be aligned at the electrode sites as required for proper use of the garment and systems described herein. Moreover, while described as a single garment, garment 50 may, in fact, be a series of pads or strips (which are identified by reference number 50s) coupled to the skin of the patient instead of a unitary garment 50. The pads may be coupled to the skin of the patient using, for example, an adhesive or the like. In the event the pads use surface electrodes instead of needle electrodes, the adhesive may be an electrically conductive adhesive. To the extent pads were used, the pads would require more instruction for proper orientation. The instruction may include pictorial direction, written direction, or a combination thereof.

Figure 5:
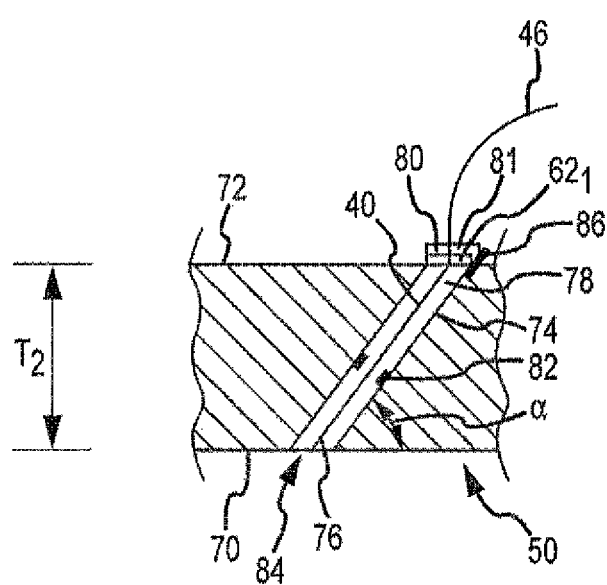
FIG. 5 is a partial cross-sectional view of the garment of FIG. 4 consistent with the technology of the present application.

Referring now to FIG. 5, a partial cross sectional view of the garment 50 is shown about an electrode site $62_1$ for example. Garment 50 may be made out of any number of materials, such as, for example, a gauze such as a KERLIX® stretch gauze glove available from Tyco Healthcare Group LP, a rubber or foam fabric, a wrap such as a COBAN® wrap available from 3M Company, a cloth fabric, a legging such as a T.E.D.® elastic stocking available from Kendall Company, or the like. Garment 50 should be capable of manipulation during surgical procedures to allow for emergencies or the like. For example, after the electrodes are positioned, garment 50 may be cut away as needed or desired during the surgical procedure. Garment 50 includes a skin surface 70 adapted to be worn adjacent to the skin 42 and a top surface 72 opposite the skin surface 70. Top surface 72 may have indicia indicative of electrode sites $62_{1-n}$ as shown in FIG. 4. Garment 50 has a thickness T from the skin surface 70 to the top surface 72. Residing in garment 50 is a capsule or tube 74. The tube 74 is shown at an acute angle $\alpha$, but the angle $\alpha$ would be dependent on the nerve being monitored/stimulated. For example, a low angle may be best for insertion of the needle electrode proximate the wrist to avoid the needle electrode actually penetrating the nerve. However, a steeper angle (possibly even approaching or in fact a 90 degree angle) may be appropriate for insertion of the needle electrode into the leg, such as for recording EMG (muscle activity). The needle electrode 40 may be provided with a lead(s) 46 or lead(s) 46 may be coupled to the needle electrode 40 just prior to or just after needle electrode 40 is advanced. The tube 74 may be a metal, metal alloy, plastic, elastomeric, gel material, or other composite of sufficient rigidity to protect the needle electrode from damage during operation and use, which includes placing the garment 50 on the patient. The needle electrode 40 has a distal end 76 adapted to pierce the skin 42 and advance through tissue until needle electrode 40 is proximate the appropriate nerve. The needle electrode 40 also has a proximate end 78 opposite the distal end 76 to which lead or leads 46 may be connected. An actuator 80, such as a plunger as shown, may be adapted to slidingly engage the tube 74 such that on actuation or depression of the actuator 80, the needle electrode 40 is advanced. Tube 74 may have a cap 81 or plug 81 about the at the proximate end 78. To the extent needle electrode 40 is not preloaded into the tube 74, the cap or plug 81 may facilitate maintaining tube 74 sterile or clean. The tube 74 may have a stop 82, such as the shoulder as shown, situated in the tube 74 to provide a positive stop for actuator 80 such that the actuator 80 can only advance the needle electrode 40 the appropriate amount. Alternatively, the bottom of tube 74 may be the stop. Tube 74 may have a cover 84 proximate the skin surface 70 of garment 50. Cover 84 at a minimum facilitates maintaining the sterility of the needle electrode 40. Cover 84 may be a penetratable surface, such as, for example, a foil, gel, rubber, or the like. Cover 84 may be relatively flat, as shown in FIG. 5, or bowed slightly, as shown in phantom in FIG. 8, to facilitate wound closure, as explained more below. Alternatively, cover 84 may be a cover that moves on actuation of actuator 80 to allow the needle electrode 40 to advance. In an exemplary embodiment, the needle electrode advances into a penetrable material, such as described below with respect to FIGS. 8 and 9, on the bottom of tube 74 that releases a skin prep fluid. The skin prep fluid may be an antimicrobial fluid that cleans and disinfects an insertion area prior to the needle electrode penetrating the skin. The initial advancement of the actuator advances the needle to penetrate the material and release the fluid, or other media, for cleaning the skin. As the actuator is further advanced, the needle electrode is subdermally advanced for placement proximate the nerve or stimulation site. At the end of the procedure, the needle electrode is actuated back at least out of the skin and possibly all the way back into tube 74 such that pressure may be returned to the penetration site to help stop any bleeding from the needle penetration. To facilitate removing the needle electrode, a retractor 86 may be operably coupled to actuator 80 such that as actuator 80 travels from surface 72 towards surface 70, retractor 86 extends from garment 50. At the termination of the procedure, retractor 86 may be inserted into garment 50 such that actuator 80, or at least needle electrode 40, reverses direction and travels toward surface 72 extracting the needle electrode 40 from the patient. Moreover, cover 84 may move such that cover 84 covers and applies pressure to the needle extraction point to inhibit or control bleeding. The garment 50 fitting snugly about the patient may supply sufficient pressure to inhibit bleeding.

Figure 6:
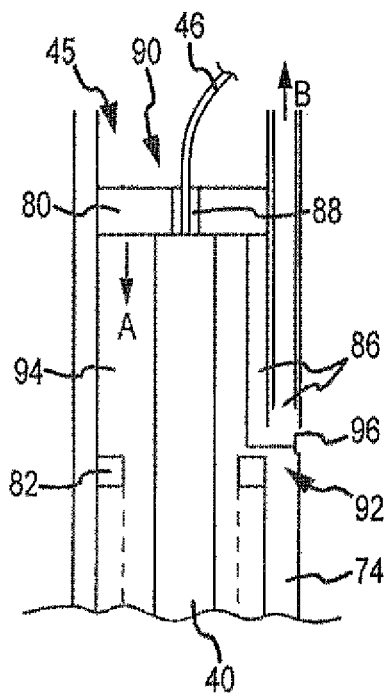
FIG. 6 is a partial cross-sectional view of the tube of FIG. 5 consistent with the technology of the present application.
Figure 7:
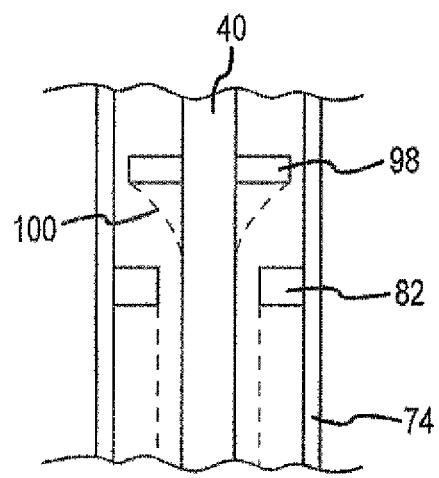
FIG. 7 is a partial cross-sectional view of the tube of FIG. 5 consistent with the technology of the present application.
Figure 8:
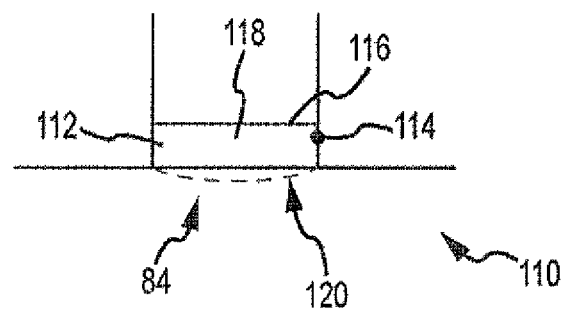
FIG. 8 is a partial cross-sectional view of the tube and cover consistent with the technology of the present application.
Figure 9:
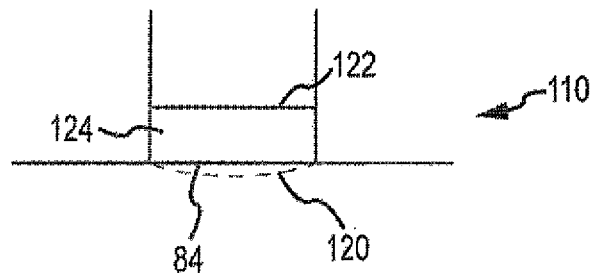
FIG. 9 is a partial cross-sectional view of the tube and cover consistent with the technology of the present application.

Referring to FIG. 6, a portion of the tube 74 with the needle electrode 40 is shown in additional detail. Needle electrode 40 is shown attached to actuator 80. Actuator 80 has a connector 88 into which that lead(s) 46 may plug. Alternatively, connector 88 may be snap fit into a bore 90 in actuator 80. In still another embodiment, lead(s) 46 may extend through the bore 90 and couple direct to needle electrode 40. Stop 82 may fit about needle electrode 40 to provide an insertion guide for needle electrode 40. In this case, stop 82 may extend to the skin surface 70 as shown in phantom. Providing a guide would facilitate placement of the needle electrode 40. The tube 74 is provided with one or more channels 92 in the tube 74. Retractor 86 extends through channel 92 and extends into needle chamber 94 of tube 74 through a port 96 in channel 92. Retractor 86 extends towards and couples with actuator 80. As actuator 80 moves in a direction A to insert needle electrode 40 into a patient, actuator 80 causes retractor 86 to correspondingly move in a direction B as shown in FIG. 6. On completion of the IOM, retractor 86 may be moved in a direction opposite to B that would correspondingly move actuator 80 in a direction opposite to A that would retract needle electrode 40 from the patient. This is but one structural example of a means to provide a retracting device on garment 50. Alternatively, actuator 80 may be under compression such that pressure (such as air pressure) in tube 74 compresses actuator 80 to maintain the needle electrode in a retracted state. For example, actuator 80 may comprise a compression spring between the plunger and a cap 81 and air pressure in tube 74 between the plunger and cover 84. As air pressure is bled from tube 74, such as, for example, out through port 96, the compression spring would advance the plunger. Thus, the decrease in pressure allows actuator 80 to expand or decompress that tends to advance needle electrode a certain distance that would correspond to the appropriate advancement of the needle electrode into the patient. In this case, the stop may the decompressed spring (i.e., fully advanced). After the procedure, pressure may be applied to tube 74 through, for example, port 96 to re-pressurize tube 74 and place actuator 80 under compression. The re-pressurization of tube 74 further may cause cover 84 to expand, as shown in FIGS. 8 and 9, to apply additional pressure to the puncture wound associated with the needle electrode penetrating the skin. Pressure may be applied via a syringe(s) or compressed air as is generally available in a hospital O.R.

While FIGS. 5 and 6 show a needle electrode 40 embedded in garment 50, the tube 74 may be provided with an opening 95 on top surface 72. In this case, the needle electrode would be provided such that it was insertable into the tube 74 from top surface 72 through the cover 84 and skin surface 70. The needle electrode may extend out of top surface 72 such that pressure may be applied to the needle electrode 40 to insert or retract the needle electrode without the need for actuator 80 and retractor 86. The needle electrode 40 in this embodiment may include a flanged surface 98 to facilitate a positive stop of the needle electrode 40 when it has been fully inserted. Alternatively, the needle electrode 40 may have a flared portion 100 as shown in phantom. In some applications, advancement of needle electrode 40 may be provided by a ratchet and pawl mechanism. In this case, for example, tube 74 may have notches 74N and protrusions 74P along tube 74 as shown in phantom in FIG. 6. The notches 74N would be sized to cooperatively engage with actuator 80 such that the needle electrode 40 may be advanced.

As mentioned above, retraction of the needle may cause bleeding at the insertion site. In one possible embodiment, the garment would be provided with a tight fit to the patient such that the garment would provide pressure to the wound site to inhibit bleeding. In some cases, however, the pressure provided by the garment alone may not be sufficient to satisfactorily promote clotting and the like. Referring now to FIG. 8, a portion 110 of tube 74 about cover 84 adjacent skin surface 70 is provided. As shown, tube 74 may terminate in a cover 84 that may be formed of a foil or the like. Alternatively, cover 84 may be similar to a diaphragm, thin rubber material, or the like. Subsequent to withdrawal of the needle electrode, an air bladder 112 may be inflated. The air bladder 112 may be inflatable by a placing a syringe (not specifically shown) in fluid communication with an intake port 114 on air bladder 112. Inflating the air bladder 112, or a balloon, provides additional pressure to the wound to facilitate clotting. A second diaphragm 116 may be used as well. Second diaphragm 116 is placed away from cover 84 such that air bladder 112 fills a space 118 between cover 84 and second diaphragm 116. In this case, cover 84 may be more elastic than diaphragm 116 so filling the air bladder causes cover 84 to expand and bow outward into a convexly curved surface 120 that further facilitates clotting. Cover 84 may be predesigned with a curved surface 120 as mentioned above.

Referring now to FIG. 9, the portion 110 of tube 74 is shown with cover 84. As mentioned above, cover 84 may be flexible allowing it to expand to provide the convex surface 112 or cover 84 may be designed with the curved surface 120 to apply pressure to the wound from the needle electrode 40. A diaphragm 122 above cover 84 defines a chamber 124. The chamber 124 contains a penetrable material 126 such as, for example, a gel, resin, composite, or the like through which the needle electrode 40 would extend. The plastic or composite material should be capable of containing a skin preparation fluid, such as, for example, a ChloraPrep®, such as is available from Medi-Flex Hospital Products Corporation Kansas, or other antimicrobial fluid as mentioned above. Collectively the above may be referred to as a cartridge. On withdrawal of the needle, the cover 84 would supply pressure to the wound site to facilitate clotting and the penetrable material would inhibit blood flow through the tube 74.

Figure 10:
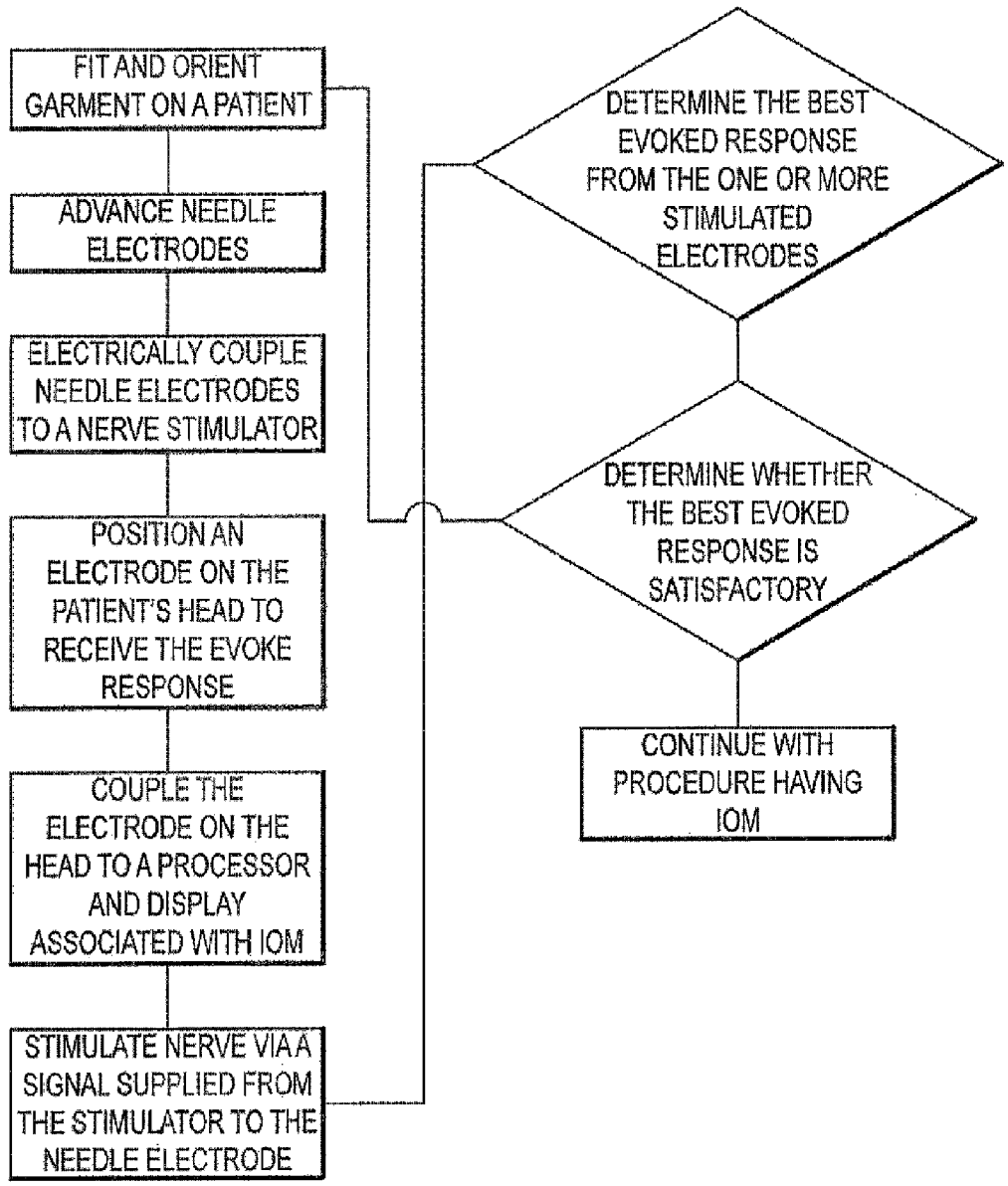
FIG. 10 is an illustrative flowchart exemplary of one method of performing operations consistent with the technology of the present application.

As provided above, garment 50 may be provided with multiple electrodes for any given IOM. Also, once advanced, even a single needle electrode would need to be tested to ensure the needle has been advanced and placed adequately to the nerve to be monitored to allow for proper system operation and the like. With the above in mind, FIG. 10 provides a flowchart 1000 with an exemplary method to identify and test placement of one or more needle electrodes 40. While flowchart 1000 is provided in certain discrete steps, one of ordinary skill in the art will recognize that the steps identified may be broken into multiple steps or multiple steps in the flowchart may be combined into a single step. Moreover, the sequence of events provided by the flowchart may be altered or rearranged without departing from the technology of the present application. In this case, flowchart 1000 relates to placing an electrode(s) to stimulate the median nerve in the arm/wrist of a patient and confirming an appropriate or satisfactory evoke potential from a electrode placed on the scalp or the like. The process begins by fitting the garment 50 on a patient, step 1002. Fitting the garment 50 may include adjusting the garment until it is properly oriented based on the indicia on the garment or separately provided instructions. Once fitted, oriented, and/or otherwise adjusted, the needle electrode(s) 40 would be advanced into the patient, step 1004. Advancing the needle electrode(s) may include actuating the actuator 80, depressing a plunger, manipulating a lever, operating a motor such as a stepper motor or the like, or physically pushing the needle electrode(s) 40 using hand pressure. If actuator 80 is under compression, advancing the needle electrode may include bleeding pressure from tube 74. In either case, the needle electrode(s) 40 are advanced through tube 74 and cover 84 into the patient. The needle electrode(s) may be advanced up to the mechanical stop in most instances such that the needle electrode(s) are proximate the associated nerve for stimulation or muscle intended for recording. In other instances, however, the needle electrode(s) may not be advanced to the mechanical stop. Lead(s) 46 would then be used to electrically couple a peripheral nerve stimulator to the electrode(s) 40, step 1006. A skin surface or subdermal electrode is positioned on the patient's head, step 1008. For example, a surface electrode may be placed about 4 cm up and 2 cm back from the top of the patient's ear. The skin surface or subdermal electrode on the patient's head is electrically coupled to a display, step 1010. The electrode(s) 40 located at the wrist, leg, etc. are stimulated by the peripheral nerve stimulator, step 1012, which is received by the electrode on the patient's head for recording, step 1014. The electrode for recording transmits a single to the recording amplifier and may be displayed on the display, step 1016. The stimulus rate is time locked to the amplifier average in order to produce the evoked response. If multiple electrodes 40 are available, each of the electrodes would be provided with the stimulation signal, in series or simultaneously. If multiple electrodes 40 are available, it is next determined which of the available electrodes 40 provides the best evoked response, step 1018. Determining the best evoked response may be done visually by observing the evoked responses on the display. For example, the best evoked response may be the evoked response that elicits the highest amplitude cortical response. Alternatively, a processor associated with the display may automatically determine the electrode 40 that provides the best evoked response. In another alternative, the impedance of each pair of electrodes at the wrist may be tested such that the pair with the lowest and most balanced impedance is selected. In other words, if only two electrodes available are placed, the system would know by the impedance that the electrode pair is the pair to stimulate through. The evoked response from the electrode 40 selected is then analyzed to determine whether the evoked response is satisfactory, step 1020. A satisfactory evoked response is generally one that has acceptable latency and amplitude parameters. If the evoked response is satisfactory, which also may be done by observing the display or automatically determined by the processor, the surgical procedure may be performed using the needle electrode 40, step 1022. If the best evoked response is not satisfactory, the garment may be adjusted, the needle electrodes adjusted, or the like and the process may be repeated until a satisfactory evoked response is obtained.

Figure 11:
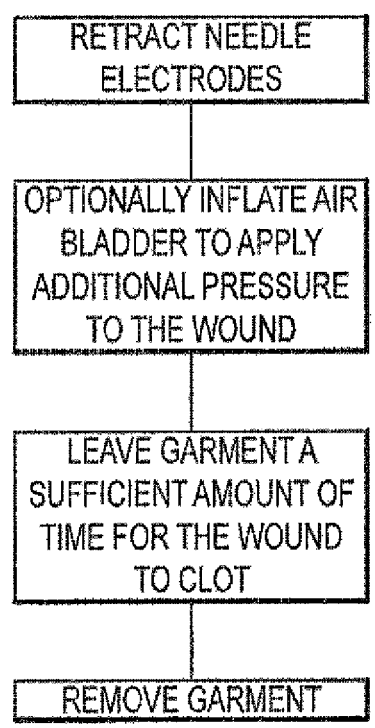
FIG. 11 is an illustrative flowchart exemplary of one method of performing operations consistent with the technology of the present application.

As mentioned above, removal of the electrode(s) 40 may cause bleeding at the insertion point. In that regard, FIG. 11 provides a flowchart 1100 with an exemplary method to identify and test placement of one or more needle electrodes 40. While flowchart 1100 is provided in certain discrete steps, one of ordinary skill in the art will recognize that the steps identified may be broken into multiple steps or multiple steps in the flowchart may be combined into a single step. Moreover, the sequence of events provided by the flowchart may be altered or rearranged without departing from the technology of the present application. In this case, after the surgical procedure is complete and IOM may be discontinued, the needle electrode(s) 40 are retracted from the patient, step 1102. The garment 50 is left in place for a sufficient amount of time to ensure the wound sites clot, step 1104. Optionally, an air bladder may be inflated using a syringe or the like to apply additional pressure to the wound, step 1103. Finally, garment 50 is removed and discarded, step 1106.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A garment to facilitate an implantation of needle electronics for intraoperative monitoring during a surgical procedure comprising:
   a fabric having a thickness separating a skin surface adapted to reside proximate to the skin of a patient and a top surface opposite the skin surface;
   at least one tube residing in the fabric between the skin surface and the top surface, the tube having a cover proximate the skin surface;
   an air bladder proximate the cover such that inflating the air bladder applies pressure to the cover and is adapted to apply pressure to a wound to facilitate clotting; and
   a needle electrode, whereby
   the tube is adapted to receive the needle electrode and the needle electrode is adapted to be inserted through the skin of the patient such that the needle electrode will be positioned proximate a nerve to be monitored.

2. The garment of claim 1 wherein the tube further comprises an actuator and a stop wherein the actuator is coupled to the needle electrode and is slidingly coupled to the tube, the actuator operatively coupled to engage the stop.

3. The garment of claim 2 wherein the actuator is a plunger.

4. The garment of claim 1 comprising a retractor coupled to the needle electrode and adapted to retract the needle electrode from a patient.

5. The garment of claim 3 further comprising an actuator coupled to the needle electrode and slidingly coupled to the tube and a port in fluid communication with an interior of the tube between the plunger and the cover, wherein the actuator comprises a plunger and a compression spring, wherein pressure in the interior of the tube may be decreased through the port to reduce the pressure such that the actuator advances the needle electrode and pressure in the interior of the tube may be increased through the port to retract the needle electrode.

6. The garment of claim 1 wherein the garment is selected from a group of garments consisting of: a glove, a wrist band, a sleeve, a shirt, a legging, a pair of pants, a cap, a body suit, or a combination thereof.

7. The garment of claim 6 wherein the fabric is selected from a group of fabrics consisting of: gauze, foam, rubber, wraps, or cloth.

8. The garment of claim 1 wherein the cover has a convexly curved surface adapted to apply pressure to a wound.

9. The garment of claim 1 further comprising a diaphragm residing in the tube that forms a chamber in which the air bladder expands when inflated.

10. The garment of claim 9 wherein the air bladder causes the cover to form a convexly curved surface.

11. The garment of claim 1 wherein the tube is formed of a material selected from the group of materials consisting of a gel material or a rubber material.

12. The garment of claim 1 further comprising a cartridge contained in the tube.

13. The garment of claim 12 wherein the cartridge comprises the cover and a diaphragm defining a chamber that is filled with a penetrable material.

14. The garment of claim 2 wherein the needle electrode comprises a surface to cooperatively engage the stop.

15. The garment of claim 14 wherein the surface is selected from a group of surfaces consisting of: a flanged surface or a flared surface.

16. A garment to facilitate an implantation of needle electrodes for intraoperative monitoring during a surgical procedure comprising:
- a fabric having a thickness separating a skin surface adapted to reside proximate to the skin of a patient and a top surface opposite the skin surface;
- at least one tube residing in the fabric between the skin surface and the top surface, the tube having a cover proximate the skin surface;
- means for applying pressure to the cover using a gas source such that inflating the means for applying pressure with a gas from the gas source is adapted to cause the cover to apply pressure to a wound to facilitate clotting;
- a needle electrode;
- means for advancing the needle electrode, and
- means for retracting the needle electrode, whereby the tube is adapted to be inserted through the skin of the patient such that the needle electrode will be positioned proximate a nerve to be monitored.

17. The garment of claim 16 wherein the means for advancing the needle electrode comprises a plunger, a compression spring, and a port in fluid communication with the tube to bleed pressure from the tube whereby the spring expands as pressure decreases to advance the needle electrode.

18. The garment of claim 17 wherein the means for retracting comprises the port in fluid communication with a fluid supply to increase pressure in the tube and compress the spring and retract the needle electrode.

19. The garment of claim 16 wherein the means for applying pressure comprises an air bladder.

20. A method of placing at least one electrode for intraoperative monitoring on a patient comprising the steps of:
- providing a garment with at least one electrode and at least one air bladder, wherein the at least one electrode is a needle electrode adapted to extend from the garment and pierce skin of a patient and the at least one air bladder is located in the garment proximal where the needle electrode extends from the garment;
- arranging the garment on the patient such that the at least one electrode is oriented for use in an intraoperative monitoring procedure and extending the needle electrode;
- performing the intraoperative monitoring procedure;
- retracting the needle electrode from the patient;
- inflating the air bladder to apply pressure where the needle electrode pierced the skin to facilitate clotting; and
- removing the garment.

\* \* \* \* \*